US00PP09293P

United States Patent [19]

van Andel

[11] Patent Number: Plant 9,293

[45] Date of Patent: Sep. 19, 1995

[54] POT FREESIA VARIETY NAMED 'VAPOPEY'

[75] Inventor: Jacob van Andel, Aalsmer, Netherlands

[73] Assignee: Van Staaveren B.V., Aalsmeer, Netherlands

[21] Appl. No.: 331,035

[22] Filed: Oct. 28, 1994

[51] Int. Cl.[6] ..... A01H 5/00

[52] U.S. Cl. ..... Plt./83

[58] Field of Search ..... Plt. 83

*Primary Examiner*—James R. Feyrer

*Attorney, Agent, or Firm*—Christie, Parker & Hale

[57] ABSTRACT

A new variety of pot freesia suitable for growing indoors as a potted plant producing light yellow flowers.

1 Drawing Sheet

BACKGROUND OF THE INVENTION

This invention relates to a new and distinct variety of freesia which originated by crossing two unpatented, unnamed varieties of my creation at the Van Staaveren b.v. Nursery in Aalsmeer the Netherlands. The female parent is identified as 86311-AP1 and the male parent is identified as 86317-AP1. The varietal demonination of the new variety is Vapopey.

SUMMARY OF THE INVENTION

Among the features which distinguish the new variety from other presently available and known commercial cultivars are the following combination of characteristics: a habit of growth which distinguishes the new variety as a plant suitable for growing in pots and referred to as a pot freesia variety reflecting its natural dwarf characteristics without need of growth retardants, and its ability to flower independent of soil temperature up to about 23° C. in about 70 to about 100 days after planting the corms.

Asexual reproduction of the new variety vegetatively by corms and cormlets in Aalsmeer, Netherlands show that the foregoing and other distinguishing characteristics are transmitted through succeeding generations.

BRIEF DESCRIPTION OF ILLUSTRATION

The accompanying photograph illustrates the new variety and shows the flowering thereof from bud to full bloom depicted in color as nearly correct as it is possible to make in a color illustration of this character. Throughout this description, color values are based upon the Colour Chart of The Royal Horticultural Society of London, England, except where common terms of color definition are employed.

DESCRIPTION OF THE NEW VARIETY

The following description is of pot freesia plants of the new cultivar grown under glass in Aalsmeer, Netherlands, during the months of August and September. Phenotyphic expression may vary with environment, cultural and climatic conditions, as well as differences and conditions in light, soil, and temperature.

PLANT

A. Form: Upright.

B. Growth:

*Height attained.*—Depending on growing temperature, about 25 to about 35 cm. The higher the temperature, the more leaves the plant produces and the longer they are at higher temperatures, the more buds are produced in a spike. The lower the light intensity the longer and weaker are the leaves. Each combination of temperature and light intensity has a special formative influence on plant shape. Measurements given herein were made on plants grown at 12° C. initially up to 24° C. at flowering time. Generally, the cooler the plants are grown, the more compact the plants will grow and more days are necessary between planting and flowering.

*Branching.*—The inflorescence bears 1 or 2 short side shoots with flower buds.

C. Flower stem:

1. *Length.*—Depending on temperature, about 25 cm to about 35 cm.
2. *Color.*—Middle green surface rough.

D. Foliage:

1. *Size.*—Width — depends on temperature and light intensity.
2. *Quantity.*—5–8 leaves, depending on growing temperature.
3. *Shape of leaf.*—Oblong with entire margins.
4. *Texture.*—Upper side — smooth.
5. *Color.*—Leaf top — 146A to 146B.
6. *Veination.*—Freesia-like.
7. *Stem color.*—Near 146A.
8. *Corm.*—Color: White with brown scales. Size: Varying with age-circumference up to about 80 mm.

THE BUD STAGE

A. Bud form: Long ovate.

B. Bud size:

*Length.*—About 45 mm.

*Diameter.*—About 15 mm.

C. Opening rate: Medium.

D. Color:

1. *When petals first divide.*—Near 2D.
2. *When petals begin to unfurl.*—Near 2D.
3. *Calyx.*—*Shape — tubular. Size — small, smooth.*

THE FLOWER STAGE

A. Inflorescence:

1. *Blooming habit.*—Intermittent.
2. *Form.*—Freesia-like.
3. *Approximately number of flowers.*—6 to 9 per spike.

4. *Borne.*—In a spike.
5. *Size.*—Diameter — about 45 mm. Depth — 60 mm.
6. *Shape.*—Cup shaped.
7. *Color tonality from a distance.*—Pale yellow.
8. *Lasting quality on plant.*—15 to 20 days depending on temperature.

B. Flower color:

1. *Flower coloration.*—Main color of inner side of the lateral outer tips, near 2D.
2. *Inner petals.*—Main color of inner side of the medium outer tips, near 12A and 23A; main color of inner side of the lateral inner tips near 12A and 17A.
3. *Outer petals.*—Main color of inner side of the medium inner tips, near 9B.
4. *Describe discoloration as bloom ages.*—Flower color darkens in shade up to orange yellow.

5. *Petals.*—Number of petals: 6. Arrangement: Tubular, imbricated.
6. *Texture.*—Soft.
7. *Shape.*—6 tips of the tube.

C. Persistence: Persist 15 to 20 days on the plant.

REPRODUCTIVE ORGANS

A. Stamens, filaments and anthers:

1. *Stamens.*—Pale yellow.
2. *Anthers.*—Color — just before opening: white.

B. Pistils:

1. *Styles.*—Yellow.
2. *Stigmas.*—Yellow.

I claim:

1. A new and distinct variety of pot freesia substantially as described and illustrated herein.

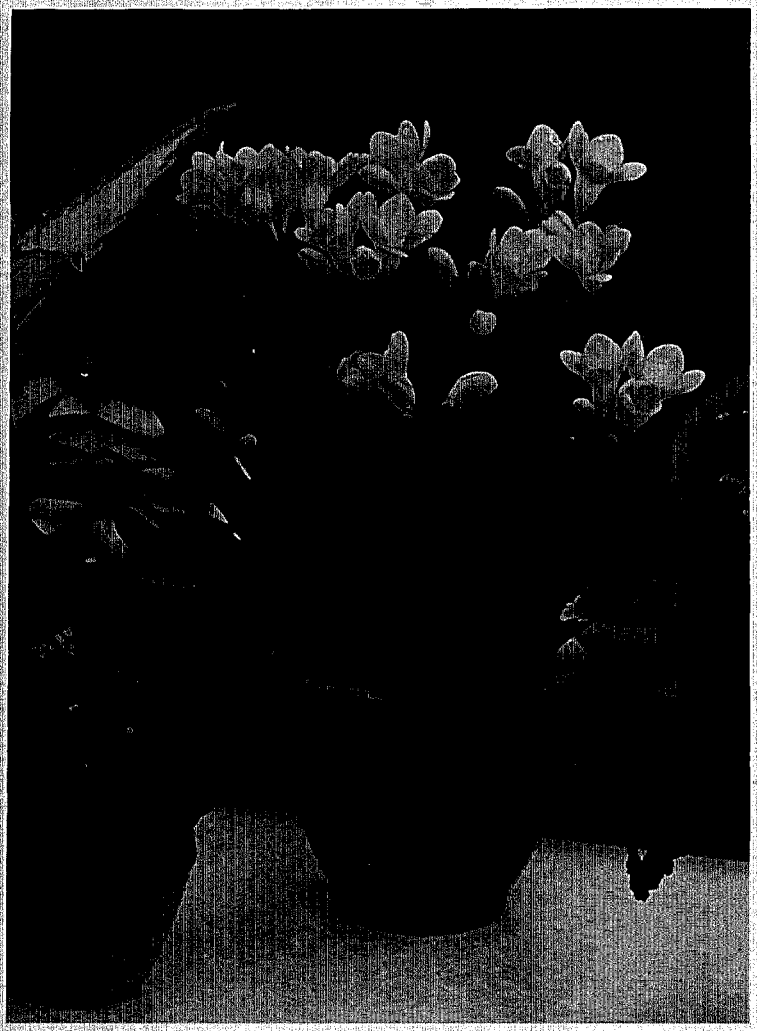

* * * * *